United States Patent [19]

Okada et al.

[11] Patent Number: 5,039,693

[45] Date of Patent: Aug. 13, 1991

[54] PYRAZOLE AMIDES AND INSECTICIDE AND MITICIDE CONTAINING THEM AS ACTIVE INGREDIENT

[75] Inventors: Itaru Okada, Kanagawa; Shuko Okui, Tokyo; Mabuko Yamaura, Iwaki; Yoji Takahashi, Machida, all of Japan

[73] Assignee: Mitsubishi Kasei Corporation, Tokyo, Japan

[21] Appl. No.: 420,466

[22] Filed: Oct. 12, 1989

[30] Foreign Application Priority Data

Oct. 14, 1988 [JP] Japan .................................. 63-258930
May 2, 1989 [JP] Japan .................................. 1-113086
Sep. 12, 1989 [JP] Japan .................................. 1-236475

[51] Int. Cl.$^5$ ........................................... A01N 43/56
[52] U.S. Cl. ...................................... 514/406; 424/405; 514/407; 514/234.5; 514/232.5; 514/316; 514/322; 546/187; 546/199; 546/14; 549/369

[58] Field of Search ..................... 514/406, 407, 234.5, 514/232.5, 316, 322; 424/405; 546/187, 199, 14; 549/369

[56] References Cited

U.S. PATENT DOCUMENTS

| | | | |
|---|---|---|---|
| 3,457,269 | 7/1969 | Kirchner | 544/271 |
| 3,567,721 | 3/1971 | Wajngurt | 544/109 |
| 4,950,668 | 8/1990 | Okada et al. | 514/407 |

FOREIGN PATENT DOCUMENTS 0307801 3/1989 European Pat. Off. .
0612674 8/1979 Switzerland .

*Primary Examiner*—Thurman K. Page
*Assistant Examiner*—Robert H. Harrison
*Attorney, Agent, or Firm*—Oblon, Spivak, McClelland, Maier & Neustadt

[57] ABSTRACT

Novel pyrazole amide and an insecticidal and miticidal composition containing the pyrazole amide as an active ingredient are described.

The pyrazole amide according to the present invention shows excellent insecticidal and miticidal activities.

9 Claims, No Drawings

PYRAZOLE AMIDES AND INSECTICIDE AND MITICIDE CONTAINING THEM AS ACTIVE INGREDIENT

BACKGROUND OF THE INVENTION

The present invention relates to novel pyrazole amides and insecticide or miticide containing them as the active ingredient.

Examples of compounds having a structure similar to that of the compound according to the present invention are described for those having bacteriocidal activity in Pest. Bio. Phy., 25, 163 (1986), Japanese Patent Application Laid-Open (KOKAI) Nos. 52-87168 and 60-34949, for those having herbicidal activity in Japanese Patent Application Laid-Open (KOKAI) No. 57-106665, for those having medicinal activity in Japanese Patent Application Laid-Open (KOKAI) Nos. 47-6269, 48-56671, 52-83840, Japanese Patent Publication No. 55-44751, Japanese Patent Application Laid-Open (KOKAI) Nos. 56-73071 and 59-95272, as well as in J. Pharm. Sci., 74, 1013 (1985). However, insecticidal or miticidal activity are not reported at all. Further, aralkyl group as the substituent on the amino group is not mentioned at all in the above-mentioned publications and literatures.

Further, there are described N-benzyl-3-methyl-5-pyrazolecarboxamide and benzyl 3-methyl-5-pyrazolecarboxylate in Farmaco, Ed. Sci., 22, 692 (1967), N-benzyl-1-(2,4-dinitrophenyl)-3-biphenyl-5-pyrazolecarboxamide in Rev. Roum. Chim., 23, 1581 (1978), N-(4-hydroxybenzyl)-1,3-dimethyl-5-pyrazolecarboxamide and N-(4-hydroxycarbonylmethoxybenzyl)-1,3-dimethyl-5-pyrazolecarboxamide in Japanese Patent Application Laid-Open (KOKAI) No. 50-58056. However, insecticidal, miticidal and bacteriocidal activities for these compounds are not reported at all.

Further, Japanese Patent Application Laid-Open (KOKAI) Nos. 63-246367 and 63-135364 describe that N-(α-cyanobenzyl)-5-pyrazolecarboxamides have bacteriocidal activity but these compounds have a feature of having a cyano group on α-position. Further, Japanese Patent Application Laid-Open (KOKAI) No. 63-91373 proposes N-(alkyl, substituted or not-substituted phenyl or benzyl)-1-(substituted or not-substituted phenyl)-5-pyrazolecarboxamide as a plant growth controlling agent and toxicity moderator. Further, Japanese Patent Application Laid-Open (KOKAI) No. 62-120369 proposes N-(substituted or not-substituted benzyl)-1-(substituted phenyl)-4-(nitro or cyano)-5-pyrazolecarboxamides. They have a feature of having a nitro or cyano group at the 4-position on the pyrazole ring, but working examples for N-(substituted or not-substituted benzyl)-5-pyrazolecarboxamides are not described at all.

Further, Japanese Patent Application Laid-Open (KOKAI) No. 63-258859 proposes N-(substituted or not-substituted aralkyl)-1-(substituted phenyl)-4-(substituted thio, substituted sulfoxy or substituted sulfonyl)-5-pyrazolecarboxamides. They have a feature of having substituted thio group, substituted sulfoxy group or substituted sulfonyl group at the 4-position on the pyrazole ring, but working examples for N-(substituted or not-substituted aralkyl)-5-pyrazolecarboxamides are not described at all. Further, it is described that N-(substituted or not-substituted benzyl)-3-methyl-4-nitro-5-pyrazolecarboxamide has a medicinal activity in Synthesis, 727 (1981); Farmaco, Ed. Sci., 38, 369 (1984) and J. Med. Chem., 27. 986 (1984). Further, it is described that N-(dibenzyl or dialkyl)-3-methyl-5-pyrazolecarboxamide has a medicinal activity in Japanese Patent Publication No. 48-15300. Japanese Patent Application Laid-Open (KOKAI) Nos. 64-25763 and 1-156964 describe those compounds having structures somewhat similar to those of the compounds according to the present invention, but they do not report at all for the compounds according to the present invention.

Since harmful insects have recently had resistance to insecticides due to use of insecticides for many years, it has been difficult to control insects by conventional insecticides. For example, insect having resistance to organophosphorous compounds and carbamate compounds which are both typical insecticides have been widely generated, resulting in the difficulty of control of these insects. In addition, the presence of insects having the resistance to synthetic pyrethloid-type insecticides which have recently attracted attention has been reported. On the other hand, some of the organophosphorous compounds or carbamate compounds exhibit high toxicity, and some of them disturb the ecological system due to their high residual effect to bring about an extremely anxious problem.

The present inventors have previously found that the compounds represented by the following structural formulae (II) and (III) show insecticidal and miticidal activity.

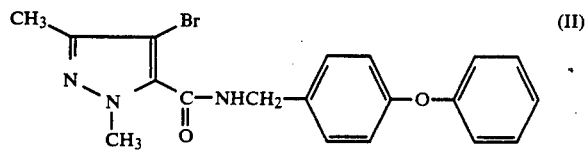

(II)

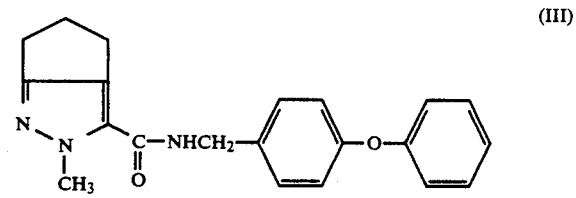

(III)

However, it has been expected for the development of novel compounds having more excellent controlling effect, lower toxicity and lower residual effect than those of the above compounds.

The present inventors have made an earnest study on novel compounds which can overcome such situation and, as a result, have accomplished the present invention based on the finding of novel pyrazoles having excellent insecticidal and miticidal activity.

SUMMARY OF THE INVENTION

In a first aspect of the present invention, there is provided pyrazole amides represented by the formula (I):

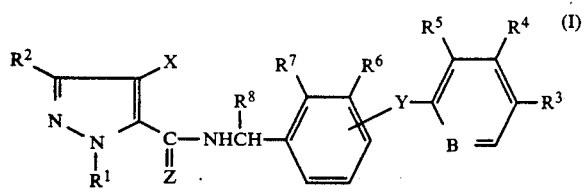

where $R^1$ represents $C_1$-$C_4$ alkyl group; $R^2$ represents hydrogen atom, $C_1$-$C_4$ alkyl group, cyclopropyl group, $C_1$-$C_4$ alkoxy group or $C_2$-$C_4$ alkylcarbonyloxy group; X represents hydrogen atom, halogen atom, $C_1$-$C_4$ alkyl group, $C_1$-$C_4$ alkoxy group, $C_1$-$C_3$ haloalkoxy group, $C_2$-$C_4$ alkylcarbonyloxy group or hydroxy group; $R^2$ and X may combine together to form

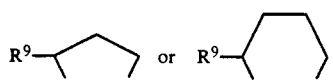

in which $R^9$ represents hydrogen atom or $C_1$-$C_3$ alkyl group; one of $R^3$, $R^4$ and $R^5$ is hydrogen atom and the others represent independently hydrogen atom, halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group of $C_3$-$C_6$ alkoxyalkoxyalkyl group; $R^3$ and $R^4$ may combine together to form

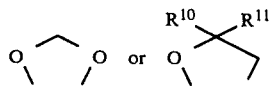

in which $R^{10}$ and $R^{11}$ represent independently hydrogen atom or $C_1$-$C_4$ alkyl group; one of $R^6$ and $R^7$ represents hydrogen atom and the other represents hydrogen atom, $C_1$-$C_4$ alkyl group, $C_1$-$C_4$ alkoxy group or halogen atom; Y represents oxygen atom, sulfur atom, sulfinyl group, sulfonyl group or carbonyl group; B represents —CH— or nitrogen atom; $R^8$ represents hydrogen atom or methyl group and Z represents oxygen atom or sulfur atom, with the proviso that all of $R^3$, $R^4$ and $R^5$ are not hydrogen atoms when Y is oxygen and B is —CH—.

In a second aspect of the present invention, there is provided an insecticidal and miticidal composition which comprises as an active ingredient an insecticidally and miticidally effective amount of the pyrazole amide represented by the formula (I), and an insecticidally or miticidally acceptable adjuvant.

In a third aspect of the present invention, there is provided a method for controlling insects and mites which comprises applying an insecticidally and miticidally effective amount of the pyrazole amide represented by the formula (I) to eggs or larvae of the insects and mites.

DETAILED DESCRIPTION OF THE INVENTION

In the formula (I), $R^1$ represents $C_1$-$C_4$ linear or branched alkyl group such as methyl group, ethyl group, n-propyl group, isopropyl group, n-butyl group, isobutyl group, sec-butyl group and t-butyl group, preferably, methyl group.

$R^2$ represents hydrogen atom; $C_1$-$C_4$ linear or branched alkyl group such as methyl group, ethyl group, n-propyl group, isopropyl group, n-butyl group, isobutyl group, sec-butyl group and t-butyl group; cyclopropyl group; $C_1$-$C_4$ linear or branched alkoxy group such as methoxy group, ethoxy group, n-propoxy group, isopropoxy group, n-butoxy group, isobutoxy group, sec-butoxy group and t-butoxy group; or $C_2$-$C_4$ linear or branched alkylcarbonyloxy group such as methylcarbonyloxy group, ethylcarbonyloxy group, n-propylcarbonyloxy group and isopropylcarbonyloxy group, preferably, hydrogen atom; $C_1$-$C_4$ linear or branched alkyl group such as methyl group, ethyl group, n-propyl group, isopropyl group, n-butyl group, isobutyl group, sec-butyl group and t-butyl group; or $C_1$-$C_3$ linear or branched alkoxy group such as methoxy group, ethoxy group, n-propoxy group and isopropoxy group.

X represents hydrogen atom; halogen atom such as fluorine atom, chlorine atom and bromine atom; $C_1$-$C_4$ linear or branched alkyl group such as methyl group, ethyl group, n-propyl group, isopropyl group, n-butyl group, isobutyl group, sec-butyl group and t-butyl group; $C_1$-$C_4$ linear or branched alkoxy group such as methoxy group, ethoxy group, n-propoxy group, isopropoxy group, n-butoxy group, isobutoxy group, sec-butoxy group and t-butoxy group; $C_1$-$C_3$ linear or branched haloalkoxy group such as monofluoromethoxy group, monochloromethoxy group, monobromomethoxy group, difluoromethoxy group, dichloromethoxy group, dibromomethoxy group, trifluoromethoxy group, trichloromethoxy group, tribromomethoxy group, chlorofluoromethoxy group, bromofluoromethoxy group, bromochloromethoxy group, 2,2,2-trifluoroethoxy group, 2,2,2-trichloroethoxy group, 2,2,2-tribromoethoxy group, 2-chloro-2,2-difluoroethoxy group, 2-bromo-2,2-difluoroethoxy group, 2,2,3,3,3-pentafluoro-n-propoxy group, 2,2,3,3-tetrafluoro-n-propoxy group and 2,2,2-trifluoroisopropoxy group; $C_2$-$C_4$ linear or branched alkylcarbonyloxy group such as methylcarbonyloxy group, ethylcarbonyloxy group, n-propylcarbonyloxy group and isopropylcarbonyloxy group; or hydroxy group, preferably, hydrogen atom; halogen atom such as fluorine atom, chlorine atom and bromine atom; $C_1$-$C_4$ linear or branched alkyl group such as methyl group, ethyl group, n-propyl group, isopropyl group, n-butyl group, isobutyl group, sec-butyl group and t-butyl group; $C_1$-$C_3$ linear or branched alkoxy group such as methoxy group, ethoxy group, n-propoxy group and isopropoxy group; or $C_1$-$C_3$ linear or branched haloalkoxy group such as monofluoromethoxy group, monochloromethoxy group, monobromomethoxy group, difluoromethoxy group, dichloromethoxy group, dibromomethoxy group, trifluoromethoxy group, trichloromethoxy group, tribromomethoxy group, chlorofluoromethoxy group, bromofluoromethoxy group, bromochloromethoxy group, 2,2,2-trifluoroethoxy group, 2,2,2-trichloroethoxy group, 2,2,2-tribromoethoxy group, 2-chloro-2,2-difluoroethoxy group, 2- bromo-2,2-difluoroethoxy group, 2,2,3,3,3-pentafluoro-n-propoxy group, 2,2,3,3-tetrafluoro-n-propoxy group and 2,2,2-trifluoroisopropoxy group.

R² and X may combine together to form

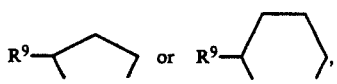

wherein R⁹ represents hydrogen atom; or $C_1$–$C_3$ linear or branched alkyl group such as methyl group, ethyl group, n-propyl group and isopropyl group.

One of R³, R⁴ and R⁵ represents hydrogen atom, and the others represent independently hydrogen atom; halogen atom such as fluorine atom, chlorine atom and bromine atom; $C_1$–$C_4$ linear or branched alkyl group such as methyl group, ethyl group, n-propyl group, isopropyl group, n-butyl group, sec-butyl group and t-butyl group; $C_1$–$C_4$ linear or branched haloalkyl group such as monofluoromethyl group, monochloromethyl group, monobromomethyl group, difluoromethyl group, dichloromethyl group, dibromomethyl group, trifluoromethyl group, trichloromethyl group, tribromomethyl group, chlorofluoromethyl group, bromofluoromethyl group, bromochloromethyl group, bromochlorofluoromethyl group, 2,2,2-trifluoroethyl group, 2,2,2-trichloroethyl group, 2,2,2-tribromoethyl group, 2-chloro-2,2-difluoroethyl group, 2-bromo 2,2-difluoroethyl group, 2,2,3,3,3-pentafluoro-n-propyl group, 2,2,3,3-tetrafluoro-n-propyl group, 2,2,2-trifluoroisopropyl group, 2,2,3,3,4,4,4-heptafluoro-n-butyl group, 2,2,3,3,4,4-hexafluoro-n-butyl group and 2,2,3,3,3-pentafluoro-sec-butyl group; $C_3$–$C_6$ cycloalkyl group such as cyclopropyl group, cyclobutyl group, cyclopentyl group and cyclohexyl group; $C_1$–$C_4$ linear or branched alkoxy group such as methoxy group, ethoxy group, n-propoxy group, isopropoxy group, n-butoxy group, isobutoxy group, sec-butoxy group and t-butoxy group; $C_1$–$C_4$ linear or branched haloalkoxy group such as monofluoromethoxy group, monochloromethoxy group, monobromomethoxy group, difluoromethoxy group, dichloromethoxy group, dibromomethoxy group, trifluoromethoxy group, tribromomethoxy group, trichloromethoxy group, chlorofluoromethoxy group, bromofluoromethoxy group, bromochloromethoxy group, bromochlorofluoromethoxy group, 2,2,2-trifluoroethoxy group, 2,2,2-trichloroethoxy group, 2,2,2-tribromoethoxy group, 2-chloro-2,2-difluoroethoxy group, 2-bromo-2,2-difluoroethoxy group, 2,2,3,3,3-pentafluoro-n-propoxy group, 2,2,3,3-tetrafluoro-n-propoxy group, 2,2,2-trifluoroisopropoxy group, 2,2,3,3,4,4,4-heptafluoro-n-butoxy group, 2,2,3,3,4,4-hexafluoro-n-butoxy group and 2,2,3,3,3-pentafluoro-sec-butoxy group; amino group; $C_1$–$C_4$ linear or branched alkylamino group such as methylamino group, ethylamino group, n-propylamino group, isopropylamino group, n-butylamino group, isobutylamino group, sec-butylamino group and t-butylamino group; $C_2$–$C_6$ linear or branched dialkylamino group such as dimethylamino group, diethylamino group, di-n-propylamino group, diisopropylamino group, methylethylamino group, methyl-n-propylamino group, methylisopropylamino group, ethyl-n-propylamino group, ethylisopropylamino group and n-propylisopropylamino group; $C_2$–$C_5$ linear or branched alkoxycarbonylamino group such as methoxycarbonylamino group, ethoxycarbonylamino group, n-propoxycarbonylamino group, isopropoxycarbonylamino group, n-butoxycarbonylamino group, isobutoxycarbonylamino group, sec-butoxycarbonylamino group and t-butoxycarbonylamino group; $C_1$–$C_4$ linear or branched alkylthio group such as methylthio group, ethylthio group, n-propylthio group, n-butylthio group, isobutylthio group, sec-butylthio group and t-butylthio group; $C_1$–$C_4$ linear or branched alkylsulfinyl group such as methylsulfinyl group, ethylsulfinyl group, n-propylsulfinyl group, isopropylsulfinyl group, n-butylsulfinyl group, isobutylsulfinyl group, sec-butylsulfinyl group and t-butylsulfinyl group; $C_1$–$C_4$ linear or branched alkylsulfonyl group such as methylsulfonyl group, ethylsulfonyl group, n-propylsulfonyl group, isopropylsulfonyl group, n-butylsulfonyl group, isobutylsulfonyl group, sec-butylsulfonyl group and t-butylsulfonyl group; $C_2$–$C_5$ linear or branched alkoxycarbonyl group such as methoxycarbonyl group, ethoxycarbonyl group, n-propoxycarbonyl group, isopropoxycarbonyl group, n-butoxycarbonyl group, isobutoxycarbonyl group, sec-butoxycarbonyl group and t-butoxycarbonyl group; $C_2$–$C_5$ linear or branched alkylcarbonyl group such as methylcarbonyl group, ethylcarbonyl group, n-propylcarbonyl group, isopropylcarbonyl group, n-butylcarbonyl group, isobutylcarbonyl group, sec-butylcarbonyl group and t-butylcarbonyl group; nitro group; cyano group; hydroxymethyl group; $C_2$–$C_4$ alkoxyalkyl group such as methoxymethyl group, ethoxymethyl group, n-propoxymethyl group, ethoxyethyl group and methoxypropyl group; or $C_3$–$C_6$ alkoxyalkoxyalkyl group such as methoxymethoxymethyl group, ethoxymethoxymethyl group, n-propoxymethoxymethyl group, methoxyethoxymethyl group, ethoxyethoxymethyl group, ethoxyethoxyethyl group and methoxyethoxypropyl group. R³ and R⁴ may combine together to form

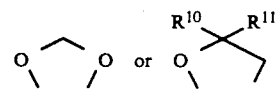

wherein R¹⁰ represent independently hydrogen atom or $C_1$–$C_4$ linear or branched alkyl group such as methyl group, ethyl group, n-propyl group, isopropyl group, n-butyl group, isobutyl group, sec-butyl group and t-butyl group.

One of R⁶ and R⁷ represents hydrogen atom and the other represents hydrogen atom; $C_1$–$C_4$ linear or branched alkyl group such as methyl group, ethyl group, n-propyl group, isopropyl group, n-butyl group, isobutyl group, sec-butyl group and t-butyl group; $C_1$–$C_4$ linear or branched alkoxy group such as methoxy group, ethoxy group, n-propoxy group, isopropoxy group, n-butoxy group, isobutoxy group, sec-butoxy group and t-butoxy group; or halogen atom such as fluorine atom, chlorine atom and bromine atom, preferably, hydrogen atom; methyl group; methoxy group; or halogen atom such as fluorine atom, chlorine atom and bromine atom.

Y represents oxygen atom, sulfur atom, sulfinyl group, sulfonyl group or carbonyl group, preferably, oxygen atom or carbonyl group.

B represents —CH— or nitrogen atom.

When Y is oxygen atom and B is —CH—, all of R³, R⁴ and R⁵ are not hydrogen atoms.

R[8] represents hydrogen atom or methyl group, and Z represents oxygen atom or sulfur atom, preferably, oxygen atom.

Preparation process for the compound according to the present invention will be explained below.

The compound according to the present invention represented by the formula (I) described above can be prepared, for example, in accordance with the following reaction scheme:

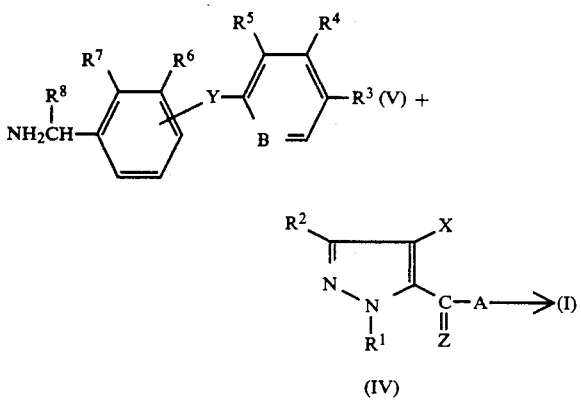

wherein R[1], R[2], R[3], R[4], R[5], R[6], R[7], R[8], X, Y, Z and B are as defined in the formula (I) described above and A represents a chlorine atom or bromine atom.

The pyrazole amide represented by the formula (I) can be obtained by reacting the compounds represented by the formulae (IV) and (V) as described above in a solvent, for example, aromatic hydrocarbon such as benzene, toluene and xylene; ketones such as acetone, methyl ethyl ketone and methyl isobutyl ketone; halogenated hydrocarbon such as chloroform and methylene chloride; water; esters such as methyl acetate and ethyl acetate; polar solvent such as tetrahydrofuran, acetonitrile, dioxane, N,N-dimethylformamide, N-methylpyrrolidone and dimethylsulfoxide at a temperature from 0° to 30° C., preferably, 0° to 5° C. under the presence of a base. As the base, there can be mentioned sodium hydroxide, potassium hydroxide, sodium carbonate, potassium carbonate, pyridine or triethylamine.

Of the compounds represented by the formula (IV), the compound in which R[2] and X combine together to form a ring can be prepared in accordance with the method described in Annalen der Chemie, Justus Liebig's, 536, 97 (1938), and the other compounds can be prepared in accordance with the method described in Bull. Soc. Chim. France, 293 (1966).

The compound represented by the formula (V) can easily be prepared by forming phenoxybenzyl bromide (or chloride) from phenoxytoluene, etc. synthesized in accordance with a method described in J. Org. Chem., 50, 3717 (1985) using bromine or chlorine by an ordinary method, imidizing with potassium phthalimide by an ordinary method and then decomposing with a hydrazine hydrate by an ordinary method.

The compound represented by the formula (I) has a remarkable controlling effect to eggs and larvae of insects such as Coleoptera, Lepidoptera, Hemiptera, Orthoptera and Diptera, as well as plant parasitic mites, with no particular restrictions thereto.

1. Hemiptera;
   Planthoppers such as *Sogatella frucifera*, *Nilaparvata lugens*, *Laodelphax striatellus*, etc.; leafhoppers such as *Nephotettix cincticeps*, *Cicadella viridis*, etc. and Aphis such as *Myzus persicae*, etc.
2. Lepidoptera;
   *Spodoptera litura*, *Chilo suppressalis*, *Cnaphalocrosis medinalis*, *Plutella xylostella*, etc.
3. Coleoptera;
   *Callosobruchus chinensis*, etc.
4. Diptera;
   *Musca domestica*, *Aedes aegypti*, *Culex pipiens molestus*, etc.
5. Spider mite;
   *Tetranychus urticae*, *Tetranychus cinnabarinus*, *Panonychus citri*, etc.

When the compound according to the present invention represented by the formula (I) is used as an insecticide or miticide, it may be used alone, or formulated into the form of emulsifiable concentrate, dust, wettable powder, solution, etc. by using an adjuvant in the same manner as conventional agricultural chemicals which is then used as it is or after dilution. As the adjuvant, those usually employed for the formulation of insecticides or miticides can be used. For instance, there can be mentioned solid carriers such as talc, kaoline, diatomaceous earth, clay and starch; water; solvent, for example, hydrocarbons such as cyclohexane, benzene, xylene and toluene, halogenated hydrocarbons such as chlorobenzene, ethers, amides such as dimethylformamide, ketones, alcohols, nitriles such as acetonitrile, and other known surface active agent such as emulsifier and dispersant.

If required, other insecticide, miticide, bacteriocide, insect growth controlling substance, plant growth controlling substance, etc. may be used in admixture or used in combination.

There is no particular restriction for the concentration of the active ingredient in the formulated insecticidal or miticidal composition and it is usually from 0.5 to 20% by weight, preferably, from 1 to 10% by weight for the dust, from 1 to 90% by weight, preferably, 10 to 80% by weight for the wettable powder, from 1 to 90% by weight, preferably, 10 to 40% by weight for the emulsifiable concentrate.

In the case of using the compound represented by the formula (I) is used as an insecticidal or miticidal agent, the active ingredient is used usually within a range of concentration from 5 to 1000 ppm, preferably, from 10 to 500 ppm.

The present invention will now be described more specifically referring to preparation examples for the compound according to the present invention, formulation examples and test examples, but it should be understood that the present invention is not restricted only to the following examples.

EXAMPLE 1

Preparation of N-[4-(4-trifluoromethylphenoxy)benzyl]-2-methyl-cyclopenta [1,2-c]-3-pyrazolecarboxamide A mixture of 1.66 g of 2-methyl-cyclopentane[1,2-c]-3-pyrazolecarboxylic acid and 11.7 g of thionyl chloride was refluxed under heating for one hour. After distilling off the thionyl chloride under a reduced pressure, the residue was dissolved in 20 ml of toluene. The solution was dropped into 25 ml of a toluene solution containing 2.67 g of 4-(4-trifluoromethylphenoxy)benzylamine and 1.21 g of triethylamine at 0°–5° C. After the completion of dropping, the mixture was stirred for 2 hours, poured into iced water and then extracted with toluene. The toluene layer was washed with an aqueous solution of sodium carbonate, water and then saturated aqueous solution of sodium chloride. After drying over anhydrous sodium sulfate, the pollution was concentrated under a reduced pressure. The residue was purified on silica gel column chromatography to obtain 3.74 g of the titled compound (No. 13) shown in Table 1.

NMR and IR for the compound were as shown below:

$^1$HNMR (CDCl$_3$) δ ppm; 2.30–2.90 (m, 6H), 4.15 (s, 3H), 4.60 (d, 2H), 6.05 (b, 1H), 7.05 (d, 4H), 7.35 (d, 2H), 7.60 (d, 2H)

IR (KBr) cm$^{-1}$; 3330, 2950, 1640, 1600, 1560, 1505, 1325, 1200, 1110, 840

EXAMPLE 2

Preparation of N-[4-(4-methylphenoxy)benzyl]-4-chloro-3-ethyl-1-methyl-5-pyrazolecarboxamide A mixture of 1.89 g of 4-chloro-3-ethyl-1-methyl-5-pyrazolecarboxylic acid and 6.0 g of thionyl chloride was refluxed under heating for one hour. After distilling off the thionyl chloride under a reduced pressure, the residue was dissolved in 10 ml of toluene. The solution was dropped into 20 ml of a toluene solution containing 2.13 g of 4-methyphenoxybenzylamine and 1.21 g of triethylamine at 0°–10° C. After the completion of dropping, the mixture was stirred for 2 hours, poured into iced water and then extracted with toluene. The toluene layer was washed with an aqueous solution of sodium carbonate, water and then saturated aqueous solution of sodium chloride. After drying over anhydrous sodium sulfate, the solution was concentrated under a reduced pressure. The residue was purified on silica gel column chromatography to obtain 3.45 g of the titled compound (No. 16) shown in Table 1.

NMR and IR for the compound were as shown below:

$^1$HNMR (CDCl$_3$) δ ppm; 1.20 (t, 3H), 2.30 (s, 3H), 2.60 (q, 2H), 4.10 (s, 3H), 4.55 (d, 2H), 6.80–7.40 (m, 9H)

IR (KBr) cm$^{-1}$; 3300, 2970, 1645, 1545, 1500, 1285, 1235, 1095, 865, 810

EXAMPLE 3

Preparation of N-(4-phenylthiobenzyl)-4-chloro-3-ethyl-1-methyl-5-pyrazole carboxamide Into 50 ml solution of ethyl acetate containing 3.50 g of 4-phenylthiobenzylamine and 2.2 g of triethylamine, was dropped 3.60 g of 4-chloro-3-ethyl-1-methyl-5-pyrazolecarboxylic acid chloride synthesized in Example 2. After the completion of dropping, the mixture was stirred for 1.5 hours, poured into iced water and then extracted with ethyl acetate. The ethyl acetate layer was washed with an aqueous solution of sodium carbonate, water and a saturated aqueous solution of sodium chloride. After drying over anhydrous sodium sulfate, the solution was concentrated under a reduced pressure. The residue was purified on silica gel column chromatography to obtain 4.70 g of the titled compound (No. 76) shown in Table 1.

NMR and IR for the compound were as shown below:

$^1$HNMR (CDCl$_3$) δ ppm; 1.23 (t, 3H), 2.63 (q, 2H), 4.15 (s, 3H), 4.60 (d, 2H), 7.10 (br, 1H), 7.20–7.50 (m, 9H)

IR (KBr) cm$^{-1}$; 3290, 2975, 1640, 1550, 1465, 1430, 1285, 1230, 1090

EXAMPLE 4

Preparation of N-[4-(3-chloro-5-trifluoromethyl-2-pyridyloxy)benzyl]-4-chloro-3-ethyl-1-methyl-5-pyrazolecarboxamide Into 50 ml solution of ethyl acetate containing 2.49 g of 4-(3-chloro-5-trifluoromethyl-2-pyridyloxy)benzylamine and 1.21 g of triethylamine, was dropped 2.07 g of 4-chloro-3-ethyl-1-methyl-5-pyrazolecarboxylic acid chloride synthesized in Example 2. After the completion of dropping, the mixture was stirred for 1 hour, poured into iced water and then extracted with ethyl acetate. The ethyl acetate layer was washed with an aqueous solution of sodium carbonate, water and a saturated aqueous solution of sodium chloride. After drying over anhydrous sodium sulfate, the solution was concentrated under a reduced pressure. The residue was purified on silica gel column chromatography to obtain 3.35 g of the titled compound (No. 75) shown in Table 1.

NMR and IR for the compound were as shown below:

$^1$HNMR (CDCl$_3$) δ ppm; 1.25 (t, 3H), 2.65 (q, 2H), 4.15 (s, 3H), 4.70 (d, 2H), 7.10 (b, 1H), 7.15 (d, 2H), 7.50 (d, 2H), 8.00 (d, 1H), 8.30 (d, 1H)

IR (KBr) cm$^{-1}$; 3290, 2980, 1635, 1545, 1455, 1320, 1290, 1160, 1125, 915, 830, 765

EXAMPLE 5

According to the procedures of Examples 1, 2, 3 and 4, the compounds shown in Tables 1, 2, 3, 4 and 5 were prepared.

TABLE 1

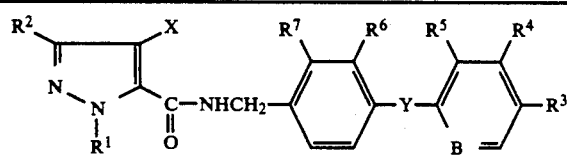

| Compound No. | $R^1$ | $R^2$ | X | $R^3$ | $R^4$ | $R^5$ | $R^6$ | $R^7$ | B | Y | m.p. (°C.) Refractive index ($n_D^{25}$) |
|---|---|---|---|---|---|---|---|---|---|---|---|
| 1 | CH$_3$ | C$_2$H$_5$ | Cl | CF$_3$ | H | H | H | H | CH | O | 121–122 |
| 2 | CH$_3$ | CH$_3$ | Cl | CF$_3$ | H | H | H | H | CH | O | 132–133 |
| 3 | CH$_3$ | CH$_3$ | Br | CF$_3$ | H | H | H | H | CH | O | 143–144 |
| 4 | CH$_3$ | CH$_3$ | CH$_3$ | CF$_3$ | H | H | H | H | CH | O | 139–140 |

TABLE 1-continued

Structure:
$R^2$ at pyrazole-3, $R^1$ on N-1, X at pyrazole-4, C(=O)-NHCH$_2$- to phenyl ($R^7$, $R^6$)-Y-phenyl ($R^5$, $R^4$, $R^3$) with ring atom B.

| No. | $R^2$ | $R^1$ | X | $R^3$ | $R^7$ | $R^6$ | $R^5$ | $R^4$ | B | Y | m.p. (°C) |
|---|---|---|---|---|---|---|---|---|---|---|---|
| 5 | CH$_3$ | cyclohexyl | | CF$_3$ | H | H | H | H | CH | O | 137–138 |
| 6 | CH$_3$ | i-C$_3$H$_7$ | Cl | CF$_3$ | H | H | H | H | CH | O | 116.5–118.5 |
| 7 | CH$_3$ | C$_2$H$_5$ | H | CF$_3$ | H | H | H | H | CH | O | 77.5–79.5 |
| 8 | CH$_3$ | H | Cl | CF$_3$ | H | H | H | H | CH | O | 94.5–95.5 |
| 9 | CH$_3$ | CH$_3$-cyclohexyl | | CF$_3$ | H | H | H | H | CH | O | 140.5–142.5 |
| 10 | CH$_3$ | C$_2$H$_5$ | F | CF$_3$ | H | H | H | H | CH | O | 63.5–64.5 |
| 11 | CH$_3$ | C$_2$H$_5$-cyclopentyl | | CF$_3$ | H | H | H | H | CH | O | 95–96 |
| 12 | CH$_3$ | C$_2$H$_5$ | Br | CF$_3$ | H | H | H | H | CH | O | 133–134 |
| 13 | CH$_3$ | cyclopentyl | | CF$_3$ | H | H | H | H | CH | O | 131–133 |
| 14 | CH$_3$ | CH$_3$-cyclopentyl | | CF$_3$ | H | H | H | H | CH | O | 74–75 |
| 15 | C$_2$H$_5$ | C$_2$H$_5$ | Cl | CF$_3$ | H | H | H | H | CH | O | 113.5–115.5 |
| 16 | CH$_3$ | C$_2$H$_5$ | Cl | CH$_3$ | H | H | H | H | CH | O | 87–88.5 |
| 17 | CH$_3$ | C$_2$H$_5$ | Br | CH$_3$ | H | H | H | H | CH | O | 109–109.5 |
| 18 | CH$_3$ | C$_2$H$_5$ | H | CH$_3$ | H | H | H | H | CH | O | 62.5–63.5 |
| 19 | CH$_3$ | CH$_3$ | CH$_3$ | CH$_3$ | H | H | H | H | CH | O | 118.5–119 |
| 20 | CH$_3$ | CH$_3$ | Cl | CH$_3$ | H | H | H | H | CH | O | 80.5–81 |
| 21 | CH$_3$ | cyclopentyl | | CH$_3$ | H | H | H | H | CH | O | 99.5–101 |
| 22 | CH$_3$ | CH$_3$-cyclopentyl | | CH$_3$ | H | H | H | H | CH | O | 95–96 |
| 23 | CH$_3$ | C$_2$H$_5$-cyclopentyl | | CH$_3$ | H | H | H | H | CH | O | 99–100 |
| 24 | CH$_3$ | C$_2$H$_5$ | Cl | C$_2$H$_5$ | H | H | H | H | CH | O | 87–88 |
| 25 | CH$_3$ | CH$_3$-cyclopentyl | | C$_2$H$_5$ | H | H | H | H | CH | O | 110.5–111.5 |
| 26 | CH$_3$ | C$_2$H$_5$ | Cl | i-C$_3$H$_7$ | H | H | H | H | CH | O | 86–87.5 |
| 27 | CH$_3$ | C$_2$H$_5$ | Cl | t-C$_4$H$_9$ | H | H | H | H | CH | O | 66.5–67.5 |
| 28 | CH$_3$ | C$_2$H$_5$ | Cl | OCH$_3$ | H | H | H | H | CH | O | 85–86.5 |
| 29 | CH$_3$ | cyclopentyl | | OCH$_3$ | H | H | H | H | CH | O | 128–129 |
| 30 | CH$_3$ | CH$_3$-cyclopentyl | | OCH$_3$ | H | H | H | H | CH | O | 110–111 |
| 31 | CH$_3$ | C$_2$H$_5$ | Cl | Oi-C$_3$H$_7$ | H | H | H | H | CH | O | 98–98.5 |
| 32 | CH$_3$ | C$_2$H$_5$ | Cl | OCHF$_2$ | H | H | H | H | CH | O | 69–70 |
| 33 | CH$_3$ | C$_2$H$_5$ | Cl | OCH$_2$CF$_3$ | H | H | H | H | CH | O | 80.5–81.5 |
| 34 | CH$_3$ | C$_2$H$_5$ | Cl | NH$_2$ | H | H | H | H | CH | O | 40–41 |
| 35 | CH$_3$ | C$_2$H$_5$ | Cl | N(CH$_3$)$_2$ | H | H | H | H | CH | O | 124–125 |
| 36 | CH$_3$ | C$_2$H$_5$ | Cl | NHn-C$_3$H$_7$ | H | H | H | H | CH | O | 68–69 |
| 37 | CH$_3$ | C$_2$H$_5$ | Cl | NHi-C$_3$H$_7$ | H | H | H | H | CH | O | Oily substance |

TABLE 1-continued

| | $R^2$ | | X | $R^7$ | $R^6$ | $R^5$ | $R^4$ | B | Y | |
|---|---|---|---|---|---|---|---|---|---|---|
| | | $R^1$ | | | | | | | | |
| 38 | CH$_3$ | C$_2$H$_5$ | Cl | N(n-C$_3$H$_7$)$_2$ | H | H | H | H | CH | O | Oily substance |
| 39 | CH$_3$ | C$_2$H$_5$ | Cl | NHCO$_2$CH$_3$ | H | H | H | H | CH | O | 106–107 |
| 40 | CH$_3$ | C$_2$H$_5$ | Cl | CO$_2$C$_2$H$_5$ | H | H | H | H | CH | O | 81–82 |
| 41 | CH$_3$ | C$_2$H$_5$ | Cl | COCH$_3$ | H | H | H | H | CH | O | 111–112.5 |
| 42 | CH$_3$ | C$_2$H$_5$ | Cl | Cl | H | H | H | H | CH | O | 110–112 |
| 43 | CH$_3$ | C$_2$H$_5$ | Cl | Cl | H | CH$_3$ | H | H | CH | O | 143.5–144.5 |
| 44 | CH$_3$ | C$_2$H$_5$ | Cl | SCH$_3$ | H | H | H | H | CH | O | 87–88 |
| 45 | CH$_3$ | CH$_3$-⟨cyclobutyl⟩ | | SCH$_3$ | H | H | H | H | CH | O | 117–118 |
| 46 | CH$_3$ | C$_2$H$_5$ | Cl | S(=O)–CH$_3$ | H | H | H | H | CH | O | 78–79 |
| 47 | CH$_3$ | C$_2$H$_5$ | Cl | SO$_2$CH$_3$ | H | H | H | H | CH | O | 107–108 |
| 48 | CH$_3$ | C$_2$H$_5$ | Cl | CN | H | H | H | H | CH | O | 105–106.5 |
| 49 | CH$_3$ | ⟨cyclobutyl⟩ | | CN | H | H | H | H | CH | O | 179–180 |
| 50 | CH$_3$ | CH$_3$-⟨cyclobutyl⟩ | | CN | H | H | H | H | CH | O | 128–129 |
| 51 | CH$_3$ | C$_2$H$_5$ | Cl | NO$_2$ | H | H | H | H | CH | O | 117–118 |
| 52 | CH$_3$ | ⟨cyclobutyl⟩ | | NO$_2$ | H | H | H | H | CH | O | 162–164 |
| 53 | CH$_3$ | CH$_3$-⟨cyclobutyl⟩ | | NO$_2$ | H | H | H | H | CH | O | $n_D^{24}$ 1.5850 |
| 54 | CH$_3$ | C$_2$H$_5$ | Cl | H | NO$_2$ | H | H | H | CH | O | 74–75 |
| 55 | CH$_3$ | C$_2$H$_5$ | Cl | H | H | NO$_2$ | H | H | CH | O | 105–106 |
| 56 | CH$_3$ | C$_2$H$_5$ | Cl | CF$_3$ | H | Cl | H | H | CH | O | 132–133 |
| 57 | CH$_3$ | ⟨cyclobutyl⟩ | | CF$_3$ | H | Cl | H | H | CH | O | 131–132 |
| 58 | CH$_3$ | CH$_3$-⟨cyclobutyl⟩ | | CF$_3$ | H | Cl | H | H | CH | O | 106–107 |
| 59 | CH$_3$ | C$_2$H$_5$ | Cl | CF$_3$ | H | H | OCH$_3$ | H | CH | O | 99–100 |
| 60 | CH$_3$ | CH$_3$-⟨cyclobutyl⟩ | | CF$_3$ | H | H | OCH$_3$ | H | CH | O | 66–67 |
| 61 | CH$_3$ | C$_2$H$_5$ | Cl | CF$_3$ | H | H | H | CH$_3$ | CH | O | 111–112 |
| 62 | CH$_3$ | CH$_3$-⟨cyclobutyl⟩ | | CF$_3$ | H | H | H | CH$_3$ | CH | O | 122–123 |
| 63 | CH$_3$ | C$_2$H$_5$ | Cl | CH$_3$ | CH$_3$ | H | H | H | CH | O | 88–89 |
| 64 | CH$_3$ | CH$_3$-⟨cyclobutyl⟩ | | CH$_3$ | CH$_3$ | H | H | H | CH | O | 110–111 |
| 65 | CH$_3$ | C$_2$H$_5$ | Cl | CH$_3$ | H | CH$_3$ | H | H | CH | O | 102–103 |
| 66 | CH$_3$ | CH$_3$-⟨cyclobutyl⟩ | | CH$_3$ | H | CH$_3$ | H | H | CH | O | 123–124 |

TABLE 1-continued

Structure:
$R^2$ at pyrazole 3-position, $X$ at pyrazole 4-position, $R^1$ on pyrazole N, carboxamide $-C(O)-NHCH_2-$ linked to phenyl bearing $R^7, R^6$, then $Y$ linking to ring B bearing $R^5, R^4, R^3$.

| No. | $R^1$ | $R^2$ | $X$ | $R^3$ | $R^4$ | $R^5$ | $R^6$ | $R^7$ | B | Y | m.p. (°C) |
|---|---|---|---|---|---|---|---|---|---|---|---|
| 67 | CH₃ | C₂H₅ | Cl | CH₃-C(OCH₃)- (methoxy isopropyl) | CH₃ | H | H | H | CH | O | 74.5–76.5 |
| 68 | CH₃ | C₂H₅ | Cl | NO₂ | CH₃ | H | H | H | CH | O | 102–103 |
| 69 | CH₃ | CH₃-cyclopentyl | | NO₂ | CH₃ | H | H | H | CH | O | Oily substance |
| 70 | CH₃ | C₂H₅ | Cl | NO₂ | OCH₃ | H | H | H | CH | O | 100–101 |
| 71 | CH₃ | C₂H₅ | Cl | NO₂ | H | F | H | H | CH | O | 102–103.5 |
| 72 | CH₃ | C₂H₅ | Cl | CF₃ | H | H | H | H | N | O | 153–154 |
| 73 | CH₃ | cyclopentyl | | CF₃ | H | H | H | H | N | O | 146–147 |
| 74 | CH₃ | CH₃-cyclopentyl | | CF₃ | H | H | H | H | N | O | 158–159 |
| 75 | CH₃ | C₂H₅ | Cl | CF₃ | H | Cl | H | H | N | O | 177–178 |
| 76 | CH₃ | C₂H₅ | Cl | H | H | H | H | H | CH | S | 81–82 |
| 77 | CH₃ | C₂H₅ | Cl | CH₃ | H | H | H | H | CH | S | 77–78 |
| 78 | CH₃ | C₂H₅ | Cl | Cl | H | H | H | H | CH | S | 95–96.5 |
| 79 | CH₃ | C₂H₅ | Cl | H | H | H | H | H | CH | S=O | 71–72 |
| 80 | CH₃ | C₂H₅ | Cl | H | H | H | H | H | CH | SO₂ | 126–127 |
| 81 | CH₃ | CH₃ | OCH₃ | CF₃ | H | H | H | H | CH | O | $n_D^{25}$ 1.5486 |
| 82 | CH₃ | CH₃ | OC₂H₅ | CF₃ | H | H | H | H | CH | O | $n_D^{25}$ 1.5428 |
| 83 | CH₃ | CH₃ | OCHF₂ | CF₃ | H | H | H | H | CH | O | 65–66 |
| 84 | CH₃ | C₂H₅ | OCH₃ | CF₃ | H | H | H | H | CH | O | $n_D^{25}$ 1.5453 |
| 85 | CH₃ | CH₃ | OH | CF₃ | H | H | H | H | CH | O | Amorphous solid |
| 86 | CH₃ | CH₃ | OCH₃ | CH₃ | H | H | H | H | CH | O | $n_D^{25}$ 1.5803 |
| 87 | CH₃ | CH₃ | OCH₃ | Cl | H | H | H | H | CH | O | $n_D^{25}$ 1.5879 |
| 88 | CH₃ | C₂H₅ | OCH₃ | CH₃ | H | H | H | H | CH | O | $n_D^{25}$ 1.5684 |
| 89 | CH₃ | $C_3H_7^i$ | H | CF₃ | H | H | H | H | CH | O | 87–87.5 |
| 91 | CH₃ | CH₃O | H | CF₃ | H | H | H | H | CH | O | 101–103 |
| 92 | CH₃ | CH₃O | Cl | CF₃ | H | H | H | H | CH | O | 98 |
| 93 | CH₃ | C₂H₅O | H | CF₃ | H | H | H | H | CH | O | 78–80 |
| 94 | CH₃ | CH₃CO- (acetyl) | H | CF₃ | H | H | H | H | CH | O | 99 |
| 95 | CH₃ | CH₃ | OC(O)CH₃ | CF₃ | H | H | H | H | CH | O | 112–113 |
| 96 | CH₃ | $C_3H_7^i$ | H | CH₃ | H | H | H | H | CH | O | 71–72 |
| 97 | CH₃ | CH₃O | Cl | CH₃ | H | H | H | H | CH | O | 74–76 |
| 98 | CH₃ | C₂H₅ | H | SCH₃ | H | H | H | H | CH | O | 70.5–71.5 |
| 99 | CH₃ | $C_3H_7^i$ | H | SCH₃ | H | H | H | H | CH | O | 74.5–75 |
| 100 | CH₃ | C₂H₅ | OCH₃ | SCH₃ | H | H | H | H | CH | O | $n_D^{25}$ 1.5993 |
| 101 | CH₃ | cyclopentyl (CH-) | | SCH₃ | CH₃ | H | H | H | CH | O | 110–111 |
| 102 | CH₃ | C₂H₅ | Cl | SC₂H₅ | H | H | H | H | CH | O | Amorphous solid |
| 103 | CH₃ | C₂H₅ | Cl | $SC_3H_7^i$ | H | H | H | H | CH | O | Amorphous solid |
| 104 | CH₃ | C₂H₅ | Cl | $S(O)_2C_3H_7^i$ | H | H | H | H | CH | O | Amorphous solid |
| 105 | CH₃ | C₂H₅ | Cl | CH₂OH | H | H | H | H | CH | O | 95–96 |

TABLE 1-continued

| No. | R² | R¹ | X | (subst) | R⁷ | R⁶ | R⁵ | R⁴ | B | Y | m.p. (°C) / $n_D$ |
|---|---|---|---|---|---|---|---|---|---|---|---|
| 106 | CH₃ | C₂H₅ | Cl | CH₂OCH₂OCH₃ | H | H | H | H | CH | O | $n_D^{25}$ 1.5749 |
| 107 | CH₃ | C₂H₅ | H | SCH₃ | CH₃ | H | H | H | CH | O | 103–104 |
| 108 | CH₃ | C₂H₅ | Cl | SCH₃ | CH₃ | H | H | H | CH | O | 88–89 |
| 109 | CH₃ | C₂H₅ | H | CH₃ | H | NO₂ | H | H | CH | O | 123–123.5 |
| 110 | CH₃ | C₂H₅ | Cl | CH₃ | H | NO₂ | H | H | CH | O | Amorphous solid |
| 111 | CH₃ | CH(CH₃)C₂H₅ |  | CH₃ | H | NO₂ | H | H | CH | O | Amorphous solid |
| 112 | CH₃ | C₂H₅ | H | NO₂ | H | CH₃ | H | H | CH | O | Amorphous solid |
| 113 | CH₃ | C₂H₅ | Cl | NO₂ | H | CH₃ | H | H | CH | O | 155.5–157.5 |
| 114 | CH₃ | CH(CH₃)C₂H₅ |  | NO₂ | H | CH₃ | H | H | CH | O | 133.5–135.5 |
| 115 | CH₃ | C₂H₅ | Cl | –OCH₂O– (R⁴,R⁵) |  | H | H | H | CH | O | 81.5–82 |
| 116 | CH₃ | CH(CH₃)C₂H₅ |  | –OCH₂O– (R⁴,R⁵) |  | H | H | H | CH | O | $n_D^{25}$ 1.5756 |
| 117 | CH₃ | C₂H₅ | H | SCH₃ | H | H | H | H | CH | S | $n_D^{25}$ 1.6329 |
| 118 | CH₃ | C₂H₅ | Cl | SCH₃ | H | H | H | H | CH | S | 96–97 |
| 119 | CH₃ | CH(CH₃)C₂H₅ |  | SCH₃ | H | H | H | H | CH | S | 117–118 |
| 120 | CH₃ | C₂H₅ | Cl | H | H | H | H | H | CH | –C(=O)– | 137–139 |
| 121 | CH₃ | C₂H₅ | Cl | Cl | H | H | H | H | CH | –C(=O)– | 112–113 |
| 122 | CH₃ | C₂H₅ | Cl | CH₃ | H | H | H | H | CH | –C(=O)– | 109.5–110.5 |
| 123 | CH₃ | C₂H₅ | Cl | CF₃ | H | H | H | H | CH | –C(=O)– | 105–106 |
| 124 | CH₃ | CH(CH₃)C₂H₅ |  | H | H | H | H | H | CH | –C(=O)– | 149–151 |
| 125 | CH₃ | CH(CH₃)C₂H₅ |  | Cl | H | H | H | H | CH | –C(=O)– | 101–103 |
| 126 | CH₃ | CH(CH₃)C₂H₅ |  | CH₃ | H | H | H | H | CH | –C(=O)– | Amorphous solid |
| 127 | CH₃ | CH(CH₃)C₂H₅ |  | CF₃ | H | H | H | H | CH | –C(=O)– | Amorphous solid |
| 128 | CH₃ | CH₃O | H | CH₃ | H | H | H | H | CH | O | $n_D^{26}$ 1.5817 |
| 129 | CH₃ | CH₃O | H | SCH₃ | H | H | H | H | CH | O | 97.5–98 |

Spectrum for No. 37
H¹ NMR (δ) (CDCl₃)
1.14–1.38(d, 6H+t, 3H) 2.64(q, 2H) 3.60(tt, 1H) 4.13(s, 3H) 4.60(d, 2H) 6.49–7.41(m, 8H)

Spectrum for No. 38
H¹ NMR (δ) (CDCl₃)
0.58–1.49(t, 6H+t, 3H) 1.50–1.80(m, 4H) 2.62(q, 2H) 3.20(t, 4H) 4.23(s, 3H) 4.60(d, 2H) 6.65–7.40(m, 8H)

TABLE 1-continued

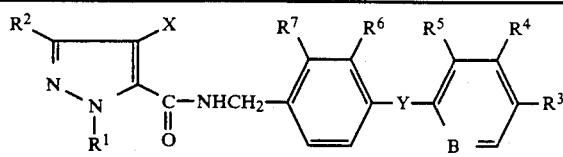

Spectrum for No. 69
H¹ NMR (δ) (CDCl₃)
1.29(d, 3H)2.54–2.87(m, 5H)3.50(m, 1H)4.18(s, 3H)4.59(d, 2H)6.08(br, 1H)6.77–7.50(m, 6H)8.10(d, 2H)
Spectrum for No. 85
H¹ NMR (δ) (CDCl₃)
4.05(s, 3H)4.57(d, 2H)6.97(d, 2H)7.01(d, 2H)7.33(d, 2H)7.57(d, 2H)8.85(br, 1H)
Spectrum for No. 90
H¹ NMR (δ) (CDCl₃)
2.05(s, 3H)4.05(s, 3H)4.57(d, 2H)6.97(d, 2H)7.01(d, 2H)7.33(d, 2H)7.57(d, 2H)8.85(bs, 1H)
Spectrum for No. 103
H¹ NMR (δ) (CDCl₃)
1.1–1.4(t, 3H+t, 3H)2.5–2.77(q, 2H+q, 2H)4.13(s, 3H)4.62(d, 2H)6.87–7.52(m, 8H)
Spectrum for No. 104
H¹ NMR (δ) (CDCl₃)
1.23(t, 3H)1.29(d, 6H)2.65(q, 2H)3.28(qq, 1H)4.14(s, 3H)4.62(d, 2H)6.87–7.12(m, 4H)7.23–7.5(m, 4H)
Spectrum for No. 105
H¹ NMR (δ) (CDCl₃)
1.21(t, 3H)1.33(d, 6H)2.64(q, 2H)3.18(qq, 1H)4.17(s, 3H)4.67(d, 2H)7.0–7.53(m, 6H)7.86(d, 2H)
Spectrum for No. 111
H¹ NMR (δ) (CDCl₃)
1.26(t, 3H)2.41(s, 3H)2,64(q, 2H)4.13(s, 3H)4.59(d, 2H)6.9–7.5(m, 7H+1H)7.73–7.84(m, 1H)
Spectrum for No. 112
H¹ NMR (δ) (CDCl₃)
1.29(d, 3H)1.9–2.2(m, 1H)2.39(s, 3H)1.5–1.82(m, 3H)3.13(m, 1H)4.16(s, 3H)4.57(d, 2H)6.04(br, 1H)6.9–7.5(m, 6H)7.73–7.83(m, 1H)
Spectrum for No. 113
H¹ NMR (δ) (CDCl₃)
1.23(t, 3H)2.42(s, 3H)2.65(q, 2H)4.15(s, 3H)4.60(d, 2H)6.36(s, 1H)6.73–7.52(m, 5H)6.52(br, 1H)7.93–8.22(m, 2H)
Spectrum for No. 127
H¹ NMR (δ) (CDCl₃)
1.30(d, 3H)1.9–2.2(m, 1H)2.42(s, 3H)2.5–2.85(m, 3H)3.15(m, 1H)4.19(s, 3H)4.70(d, 2H)6.20(br, 1H)7.2–7.9(m, 8H)
Spectrum for No. 128
H¹ NMR (δ) (CDCl₃)
1.3(d, 3H)1.7–2.2(m, 1H)2.5–2.9(m, 3H)3.2(q, 1H)4.2(s, 3H)4.71(d, 2H)6.2(br, 1H)7.48–8.0(m, 8H)

TABLE 2

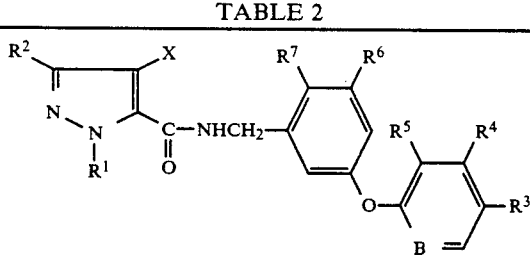

| Compound No. | $R^1$ | $R^2$ | X | $R^3$ | $R^4$ | $R^5$ | $R^6$ | $R^7$ | B | m.p. (°C.) |
|---|---|---|---|---|---|---|---|---|---|---|
| 130 | CH₃ | C₂H₅ | Cl | Cl | H | H | H | H | CH | 99–100.5 |
| 131 | CH₃ | C₂H₅ | Cl | CF₃ | H | H | H | H | CH | 75–76 |
| 132 | CH₃ | CH₃-⟨cyclopentyl⟩ | | CF₃ | H | H | H | H | CH | 103–104 |
| 133 | CH₃ | C₂H₅ | Cl | NO₂ | H | H | H | H | CH | 114–115 |
| 134 | CH₃ | C₂H₅ | Cl | CN | H | H | H | H | CH | 126–127 |
| 135 | CH₃ | C₂H₅ | Cl | H | CF₃ | H | H | H | CH | 76.5–78 |

TABLE 3

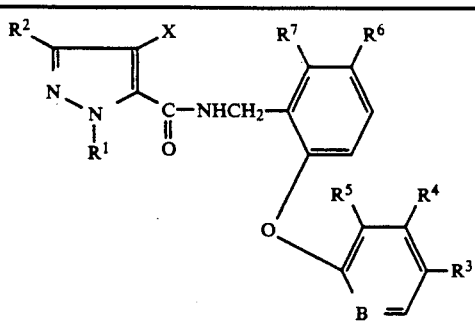

| Compound No. | R¹ | R² | X | R³ | R⁴ | R⁵ | R⁶ | R⁷ | B | m.p. (°C.) |
|---|---|---|---|---|---|---|---|---|---|---|
| 136 | $CH_3$ | $C_2H_5$ | Cl | $NO_2$ | $CH_3$ | H | H | H | CH | 92–93 |

TABLE 4

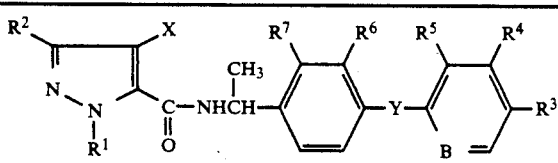

| Compound No. | R¹ | R² | X | R³ | R⁴ | R⁵ | R⁶ | R⁷ | B | Y | m.p. (°C.) Refractive index ($n_D^{25}$) |
|---|---|---|---|---|---|---|---|---|---|---|---|
| 90 | $CH_3$ | $C_2H_5$ | $OCH_3$ | $CF_3$ | H | H | H | H | CH | O | $n_D^{25}$ 1.5367 |
| 137 | $CH_3$ | $C_2H_5$ | Cl | $CF_3$ | H | H | H | H | CH | O | 81–82 |
| 138 | $CH_3$ | $CH_3$-cyclobutyl | | $CF_3$ | H | H | H | H | CH | O | 126–128[1] |
| 139 | $CH_3$ | $CH_3$-cyclobutyl | | $CF_3$ | H | H | H | H | CH | O | 131–133[1] |
| 140 | $CH_3$ | $C_2H_5$ | Cl | $SO_2CH_3$ | H | H | H | H | CH | O | 115–116 |
| 141 | $CH_3$ | $C_2H_5$ | H | $SO_2CH_3$ | H | H | H | H | CH | O | 158.5–159 |
| 142 | $CH_3$ | $CH_3$-cyclobutyl | | $SO_2CH_3$ | H | H | H | H | CH | O | 138.–140 |

[1] No. 138, No. 139 are diastrereomers, and No. 138 shows higher Rf value in TLC (thin layer chromatography).

TABLE 5

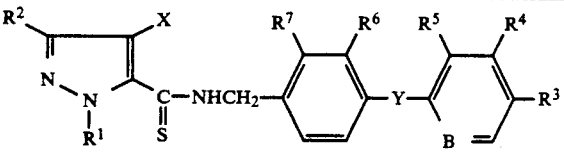

| Compound No. | R¹ | R² | X | R³ | R⁴ | R⁵ | R⁶ | R⁷ | B | Y | m.p. (°C.) Refractive index ($n_D^{25}$) |
|---|---|---|---|---|---|---|---|---|---|---|---|
| 143 | $CH_3$ | $C_2H_5$ | H | $CF_3$ | H | H | H | H | CH | O | $n_D^{25}$ 1.5813 |
| 144 | $CH_3$ | $C_2H_5$ | Cl | $CF_3$ | H | H | H | H | CH | O | $n_D^{25}$ 1.5912 |
| 145 | $CH_3$ | $CH_3$-cyclobutyl | | $CF_3$ | H | H | H | H | CH | O | 137–138 |

Formulation examples of the composition according to the present invention are shown below. "Parts" and "%" means "parts by weight" and "% by weight", respectively.

FORMULATION EXAMPLE 1

Wettable Powder

Each 20 parts of the compounds according to the present invention shown in Tables 1, 2, 3, 4 and 5, 20 parts of Carplex #80 (trade name of products manufactured by Shionogi Seiyaku Co.), 55 parts of N,N-Kaoline Clay (trade name of products manufactured by Tsuchiya Kaolin Co.), and 5 parts of higher alcohol sulfuric acid ester type surface active agent Sorpol 8070 (trade name of products manufactured by Toho Kagaku Co.) were blended and uniformly mixed and pulverized to obtain each wettable powder containing 40% of each active ingredient.

FORMULATION EXAMPLE 2

Dust

Each 2 parts of the compounds according to the present invention shown in Tables 1, 2, 3, 4 and 5, 93 parts of clay (manufactured by Nippon Talc Co.) and 5 parts of white carbon were uniformly mixed and pulverized to obtain each dust containing 2% of each active ingredient.

FORMULATION EXAMPLE 3

Emulsifiable Concentrate

Each 20 parts of the compounds according to the present invention shown in Tables 1, 2, 3, 4 and 5 was dissolved in a mixed solvent comprising 35 parts of xylene and 30 parts of dimethyl formamide, to which 15 parts of polyoxyethylene type surface active agent Sorpol 3005X (trade name of products manufactured by Toho Kagaku Co.) was added to prepare each emulsifiable concentrate containing 20% of each active ingredient.

FORMULATION EXAMPLE 4

Flowable Agent

Each 30 parts of the compounds according to the present invention as shown in Tables 1, 2, 3, 4 and 5, and previously mixed 8 parts of ethylene glycol, 5 parts of Sorpol AC3032 (trade name of products manufactured by Toho Kagaku Co.) and 0.1 parts of xanthane gum were well mixed and dispersed into 56.9 parts of water. Then, the slurry-like mixture was wet-pulverized in a DYNO-MILL (Shinmaru Enterprises Co.) to obtain each stable flowable agent containing 30% of each active ingredient.

TEST EXAMPLE 1

Effect on adult *Tetranychus urticae*

Tens adult female *Tetranychus urticae* were put on a leaf disc (2 cm diameter) of kidney beans. Then, each composition of the present invention formulated in accordance with the procedures in Formulation Example 1 was diluted with water to a predetermined concentration and 5 ml of the solution was sprayed over the leaf disc by using a rotary type scattering tower (manufactured by Mizuho Rika Co.). Test was made twice for one concentration.

Twenty four hours after the treatment, the number of alive and dead adult was counted to determine miticidal activity (%).

$$\text{Miticidal Activity (\%)} = \frac{\text{Number of dead adult}}{\text{Number of treated adult}} \times 100$$

The results are shown in Table 6. The compound No. corresponds to that in Tables 1, 4 and 5.

TEST EXAMPLE 2

Effect on eggs of *Tetranychus urticae*

Five female adult *Tetranychus urticae* were put on a leaf disc (2 cm diameter) of a kidney bean leaf. The mites were allowed to oviposit on the leaf disc for 20 hours after putting and then the adult females mites were removed. Then, 5 ml of a solution, prepared by diluting each of insecticidal and miticidal compositions of the present invention formulated in accordance with the preparation of Formulation Example 1 with water to a predetermined concentration, was scattered by using a rotary type scattering tower (manufactured by Mizuho Rika Co.). Test was made twice for each concentration.

The number of unhatched eggs and the number of hatched larvae were counted 5 days after the treatment to determine the ovicidal activity (%) by the following equation.

$$\text{Ovicidal Activity (\%)} = \frac{\text{Number of unhatched eggs}}{\text{Number of treated eggs}} \times 100$$

The results are shown in Table 6. The compound No. corresponds to that in Tables 1, 4 and 5.

TABLE 6

| Compound No. | Concentration (ppm) | Miticidal Activity (%) | Ovicidal Activity (%) |
|---|---|---|---|
| 4 | 500 | 100 | 100 |
| 5 | 500 | 100 | 100 |
| 7 | 500 | 100 | 100 |
| 8 | 500 | 100 | 100 |
| 9 | 500 | 100 | 100 |
| 10 | 500 | 100 | 100 |
| 11 | 500 | 100 | 100 |
| 13 | 500 | 100 | 100 |
| 14 | 500 | 100 | 100 |
| 32 | 500 | 100 | 100 |
| 45 | 500 | 100 | 100 |
| 46 | 500 | 100 | 100 |
| 47 | 500 | 100 | 100 |
| 51 | 500 | 100 | 100 |
| 53 | 500 | 100 | 100 |
| 60 | 500 | 100 | 100 |
| 62 | 500 | 100 | 100 |
| 81 | 500 | 100 | 100 |
| 84 | 500 | 100 | 100 |
| 86 | 500 | 100 | 100 |
| 89 | 500 | 100 | 100 |
| 91 | 500 | 100 | 100 |
| 98 | 500 | 100 | 100 |
| 99 | 500 | 100 | 100 |
| 100 | 500 | 100 | 100 |
| 102 | 500 | 100 | 100 |
| 103 | 500 | 100 | 100 |
| 108 | 500 | 100 | 100 |
| 117 | 500 | 100 | 100 |
| 118 | 500 | 100 | 100 |
| 139 | 500 | 100 | 100 |
| 145 | 500 | 100 | 100 |

TEST EXAMPLE 3

The insecticidal and miticidal activities were investigated by changing the concentration of the compounds (II) and (III) and the compounds Nos. 10, 13, 14, 60, 62, 84, 103 and 118 as shown in Table 7. The results are shown in Table 7. The compound No. corresponds to that in Table 1.

TABLE 7

| Compound No. | Concentration (ppm) | Miticidal Activity (%) | Ovicidal Activity (%) |
|---|---|---|---|
| II | 500 | 30 | 25 |
|  | 200 | 0 | 0 |
|  | 50 | 0 | 0 |
|  | 12.5 | 0 | 0 |
|  | 3.1 | 0 | 0 |
| III | 500 | 23 | 11 |
|  | 200 | 0 | 0 |
|  | 50 | 0 | 0 |
|  | 12.5 | 0 | 0 |
|  | 3.1 | 0 | 0 |
| 10 | 500 | 100 | 100 |
|  | 200 | 100 | 100 |
|  | 50 | 100 | 100 |
|  | 12.5 | 100 | 100 |
|  | 3.1 | 86 | 100 |
| 13 | 500 | 100 | 100 |
|  | 200 | 100 | 100 |
|  | 50 | 100 | 100 |
|  | 12.5 | 100 | 92 |
|  | 3.1 | 96 | 80 |
| 14 | 500 | 100 | 100 |
|  | 200 | 100 | 100 |

TABLE 7-continued

| Compound No. | Concentration (ppm) | Miticidal Activity (%) | Ovicidal Activity (%) |
| --- | --- | --- | --- |
|  | 50 | 100 | 100 |
|  | 12.5 | 100 | 98 |
|  | 3.1 | 100 | 87 |
| 60 | 500 | 100 | 100 |
|  | 200 | 100 | 100 |
|  | 50 | 100 | 100 |
|  | 12.5 | 100 | 100 |
|  | 3.1 | 100 | 73 |
| 62 | 500 | 100 | 100 |
|  | 200 | 100 | 100 |
|  | 50 | 100 | 100 |
|  | 12.5 | 100 | 100 |
|  | 3.1 | 100 | 97 |
| 84 | 500 | 100 | 100 |
|  | 200 | 100 | 100 |
|  | 50 | 100 | 100 |
|  | 12.5 | 100 | 100 |
|  | 3.1 | 100 | 100 |
| 103 | 500 | 100 | 100 |
|  | 200 | 100 | 100 |
|  | 50 | 100 | 100 |
|  | 12.5 | 100 | 85 |
|  | 3.1 | 100 | 47 |
| 118 | 500 | 100 | 100 |
|  | 200 | 100 | 100 |
|  | 50 | 100 | 100 |
|  | 12.5 | 100 | 100 |
|  | 3.1 | 90 | 100 |

TEST EXAMPLE 4

Effect on larvae of *Nilaparvata lugens*

Germinated seedlings of rice plant were set to a glass cylinder (3 cm diameter, 17 cm length) and five larvae of fourth instar of *Nilaparvata lugens* were put to them. Then, each of the insecticidal and miticidal compositions according to the present invention formulated in accordance with the preparation of Formulation Example 3 was diluted with water and scattered by 0.5 ml using a scattering tower (manufactured by Mizuho Rika Co.). Test was repeated four times for each concentration. Twenty-four hours after the treatment, the number of dead larvae was counted to determine the mortality (%). The results are shown in Table 8. The compound No. corresponds to that in Tables 1, 2 and 4.

$$\text{Mortality (\%)} = \frac{\text{Number of dead larvae}}{\text{Number of treated larvae}} \times 100$$

TEST EXAMPLE 5

Effect on larvae of *Plutella xylostella*

Slices of cabbage leaves (5×5 cm) were immersed for one minute in a water-diluted solution of each of the insecticidal and miticidal compositions of the present invention formulated in accordance with the preparation of Formulation Example 1. They were air-dried after immersion and placed in a plastic cup (7 cm diameter), to which five larvae of third instar of *Plutella xylostella* were put. Test was repeated twice for each concentration.

Two days after putting, the number of dead larvae was counted to determined the mortality (%).

The results are shown in Table 8. The compound No. corresponds to that in Tables 1, 2 and 4.

TABLE 8

| Compound No. | Concentration (ppm) | Mortality (%) Nilaparvata lugens | Mortality (%) Plutella xylostella |
| --- | --- | --- | --- |
| 1 | 500 | 100 | 100 |
| 2 | 500 | 100 | 100 |
| 3 | 500 | 100 | 100 |
| 4 | 500 | 100 | 100 |
| 5 | 500 | 100 | 100 |
| 7 | 500 | 100 | 100 |
| 8 | 500 | 100 | 100 |
| 9 | 500 | 100 | 100 |
| 10 | 500 | 100 | 100 |
| 11 | 500 | 100 | 100 |
| 12 | 500 | 100 | 100 |
| 13 | 500 | 100 | 100 |
| 14 | 500 | 100 | 100 |
| 16 | 500 | 100 | 100 |
| 17 | 500 | 100 | 100 |
| 19 | 500 | 100 | 100 |
| 20 | 500 | 100 | 100 |
| 21 | 500 | 100 | 100 |
| 22 | 500 | 100 | 100 |
| 24 | 500 | 100 | 100 |
| 25 | 500 | 100 | 100 |
| 28 | 500 | 100 | 100 |
| 30 | 500 | 100 | 100 |
| 32 | 500 | 100 | 100 |
| 33 | 500 | 100 | 100 |
| 39 | 500 | 100 | 100 |
| 41 | 500 | 100 | 100 |
| 42 | 500 | 100 | 100 |
| 44 | 500 | 100 | 100 |
| 45 | 500 | 100 | 100 |
| 46 | 500 | 100 | 100 |
| 47 | 500 | 100 | 100 |
| 48 | 500 | 100 | 100 |
| 50 | 500 | 100 | 100 |
| 51 | 500 | 100 | 100 |
| 52 | 500 | 100 | 100 |
| 53 | 500 | 100 | 100 |
| 58 | 500 | 100 | 100 |
| 60 | 500 | 100 | 100 |
| 62 | 500 | 100 | 100 |
| 63 | 500 | 100 | 100 |
| 65 | 500 | 100 | 100 |
| 67 | 500 | 100 | 100 |
| 68 | 500 | 100 | 100 |
| 69 | 500 | 100 | 100 |
| 71 | 500 | 100 | 100 |
| 73 | 500 | 100 | 100 |
| 74 | 500 | 100 | 100 |
| 81 | 500 | 100 | 100 |
| 84 | 500 | 100 | 100 |
| 87 | 500 | 100 | 100 |
| 88 | 500 | 100 | 100 |
| 89 | 500 | 100 | 100 |
| 90 | 500 | 100 | 100 |
| 91 | 500 | 100 | 100 |
| 98 | 500 | 100 | 100 |
| 99 | 500 | 100 | 100 |
| 100 | 500 | 100 | 100 |
| 102 | 500 | 100 | 100 |
| 116 | 500 | 100 | 100 |
| 117 | 500 | 100 | 100 |
| 118 | 500 | 100 | 100 |
| 121 | 500 | 100 | 100 |
| 123 | 500 | 100 | 100 |
| 125 | 500 | 100 | 100 |
| 131 | 500 | 100 | 100 |
| 133 | 500 | 100 | 100 |
| 137 | 500 | 100 | 100 |
| 139 | 500 | 100 | 100 |

TEST EXAMPLE 6

Insecticidal and miticidal activities were investigated by changing the concentration of the compounds (II) and (III), and the compounds Nos. 4, 10, 13, 14, 44, 47, 48, 60, 62, 68, 81, 84, 98, 100, 131 and 139 as shown in Table 9. The results are shown in Table 9. The compound No. corresponds to that in Table 1, 2 and 4.

TABLE 9

| Compound No. | Concentration (ppm) | Mortality (%) Nilpaarvata lugens | Mortality (%) Plutella xylostella |
|---|---|---|---|
| II | 500 | 90 | 50 |
|  | 200 | 70 | 0 |
|  | 50 | 20 | 0 |
|  | 12.5 | 0 | 0 |
|  | 3.1 | 0 | 0 |
| III | 500 | 100 | 100 |
|  | 200 | 100 | 100 |
|  | 50 | 100 | 80 |
|  | 12.5 | 80 | 10 |
|  | 3.1 | 30 | 0 |
| 4 | 500 | 100 | 100 |
|  | 200 | 100 | 100 |
|  | 50 | 100 | 100 |
|  | 12.5 | 100 | 100 |
|  | 3.1 | 100 | 65 |
| 10 | 500 | 100 | 100 |
|  | 200 | 100 | 100 |
|  | 50 | 100 | 95 |
|  | 12.5 | 100 | 0 |
|  | 3.1 | 80 | 0 |
| 13 | 500 | 100 | 100 |
|  | 200 | 100 | 100 |
|  | 50 | 100 | 100 |
|  | 12.5 | 100 | 30 |
|  | 3.1 | 85 | 0 |
| 14 | 500 | 100 | 100 |
|  | 200 | 100 | 100 |
|  | 50 | 100 | 100 |
|  | 12.5 | 100 | 100 |
|  | 3.1 | 100 | 100 |
| 44 | 500 | 100 | 100 |
|  | 200 | 100 | 100 |
|  | 50 | 100 | 100 |
|  | 12.5 | 90 | 100 |
|  | 3.1 | 80 | 95 |
| 47 | 500 | 100 | 100 |
|  | 200 | 100 | 100 |
|  | 50 | 100 | 100 |
|  | 12.5 | 90 | 100 |
|  | 3.1 | 70 | 90 |
| 48 | 500 | 100 | 100 |
|  | 200 | 100 | 100 |
|  | 50 | 100 | 100 |
|  | 12.5 | 100 | 100 |
|  | 3.1 | 85 | 100 |
| 60 | 500 | 100 | 100 |
|  | 200 | 100 | 100 |
|  | 50 | 100 | 100 |
|  | 12.5 | 90 | 50 |
|  | 3.1 | 90 | 10 |
| 62 | 500 | 100 | 100 |
|  | 200 | 100 | 100 |
|  | 50 | 100 | 100 |
|  | 12.5 | 100 | 100 |
|  | 3.1 | 100 | 75 |
| 68 | 500 | 100 | 100 |
|  | 200 | 100 | 100 |
|  | 50 | 100 | 100 |
|  | 12.5 | 70 | 100 |
|  | 3.1 | 30 | 100 |
| 81 | 500 | 100 | 100 |
|  | 200 | 100 | 100 |
|  | 50 | 100 | 100 |
|  | 12.5 | 100 | 50 |
|  | 3.1 | 90 | 0 |
| 84 | 500 | 100 | 100 |
|  | 200 | 100 | 100 |
|  | 50 | 100 | 100 |
|  | 12.5 | 100 | 100 |
|  | 3.1 | 85 | 95 |
| 98 | 500 | 100 | 100 |
|  | 200 | 100 | 100 |
|  | 50 | 100 | 100 |
|  | 12.5 | 100 | 100 |
|  | 3.1 | 36 | 100 |
| 100 | 500 | 100 | 100 |
|  | 200 | 100 | 100 |
|  | 50 | 100 | 100 |
|  | 12.5 | 100 | 100 |
|  | 3.1 | 90 | 100 |
| 131 | 500 | 100 | 100 |
|  | 200 | 100 | 100 |
|  | 50 | 100 | 100 |
|  | 12.5 | 100 | 100 |
|  | 3.1 | 90 | 95 |
| 139 | 500 | 100 | 100 |
|  | 200 | 100 | 100 |
|  | 50 | 100 | 100 |
|  | 12.5 | 100 | 100 |
|  | 3.1 | 90 | 100 |

What is claimed is:

1. A pyrazole amide represented by the following formula (I):

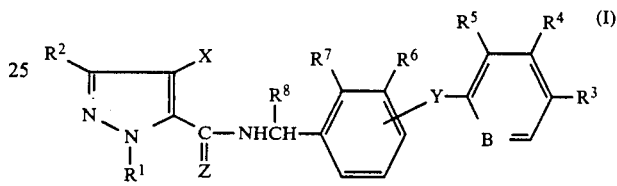

where $R^1$ represents $C_1$-$C_4$ alkyl group; $R^2$ represents hydrogen atom, $C_1$-$C_4$ alkyl group, cyclopropyl group, $C_1$-$C_4$ alkoxy group or $C_2$-$C_4$ alkylcarbonyl group; X represents hydrogen atom, halogen atom, $C_1$-$C_4$ alkyl group, $C_1$-$C_4$ alkoxy group, $C_1$-$C_3$ haloalkoxy group, $C_2$-$C_4$ alkylcarbonyloxy group or hydroxy group; $R^2$ and X may combine together to form

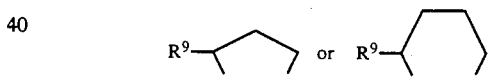

in which $R^9$ represents hydrogen atom or $C_1$-$C_3$ alkyl group; one of $R^3$, $R^4$ and $R^5$ is hydrogen atom and the others represent independently hydrogen atom, halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group and $C_3$-$C_6$ alkoxyalkoxyalkyl group; $R^3$ and $R^4$ may combine together to form

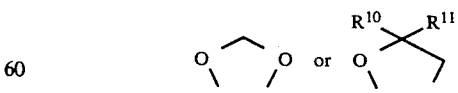

in which $R^{10}$ and $R^{11}$ represent independently hydrogen atom or $C_1$-$C_4$ alkyl group; one of $R^6$ and $R^7$ represents hydrogen atom and the other represents hydrogen atom, $C_1$-$C_4$ alkyl group, $C_1$-$C_4$ alkoxy group or halogen atom; Y represents oxygen atom, sulfur atom, sulfinyl group, sulfonyl group or carbonyl group; B represents —CH— or nitrogen atom; $R^8$ represents hydrogen atom or methyl group and Z represents oxygen atom or sulfur atom, with the proviso that all of $R^3$, $R^4$ and $R^5$ are not hydrogen atoms when Y is oxygen and B is —CH—.

2. The pyrazole amide according to claim 1, wherein $R^1$ is methyl group; $R^2$ represents hydrogen atom, $C_1$-$C_4$ alkyl group or $C_1$-$C_3$ alkoxy group; X represents hydrogen atom, halogen atom, $C_1$-$C_4$ alkyl group, $C_1$-$C_3$ alkoxy group or $C_1$-$C_3$ haloalkoxy group; $R^2$ and X may combine together to form:

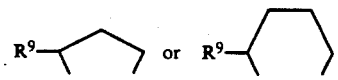

in which $R^9$ represents hydrogen atom or $C_1$-$C_3$ alkyl group; one of $R^6$ and $R^7$ represents hydrogen atom and the other represents hydrogen atom, methyl group, methoxy group or halogen atom; Y represents oxygen atom or carbonyl group and Z represents oxygen atom.

3. An insecticidal and miticidal composition which comprises as an active ingredient an insecticidally and miticidally effective amount of a pyrazole amide represented by the formula (I):

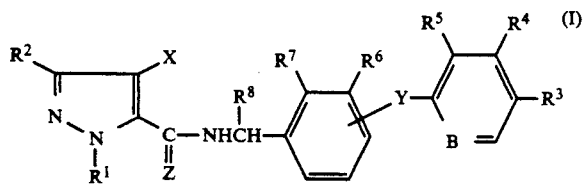

where $R^1$ represents $C_1$-$C_4$ alkyl group; $R^2$ represents hydrogen atom, $C_1$-$C_4$ alkyl group, cyclopropyl group, $C_1$-$C_4$ alkoxy group or $C_2$-$C_4$ alkylcarbonyloxy group; X represents hydrogen atom, halogen atom, $C_1$-$C_4$ alkyl group, $C_1$-$C_4$ alkoxy group, $C_1$-$C_3$ haloalkoxy group, $C_2$-$C_4$ alkylcarbonyloxy group or hydroxy group; $R^2$ and X may combine together to form

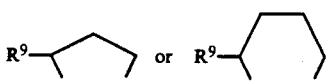

in which $R^9$ represents hydrogen atom or $C_1$-$C_3$ alkyl group; one of $R^3$, $R^4$ and $R^5$ is hydrogen atom and the others represent independently hydrogen atom, halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group or $C_3$-$C_6$ alkoxyalkoxyalkyl group; $R^3$ and $R^4$ may combine together to form

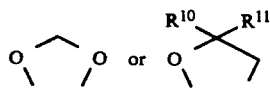

in which $R^{10}$ and $R^{11}$ represent independently hydrogen atom or $C_1$-$C_4$ alkyl group; one of $R^6$ and $R^7$ represents hydrogen atom and the other represents hydrogen atom, $C_1$-$C_4$ alkyl group, $C_1$-$C_4$ alkoxy group or halogen atom; Y represents oxygen atom, sulfur atom, sulfinyl group, sulfonyl group or carbonyl group; B represents —CH— or nitrogen atom; $R^8$ represents hydrogen atom or methyl group and Z represents oxygen atom or sulfur atom, with the proviso that all of $R^3$, $R^4$ and $R^5$ are not hydrogen atoms when Y is oxygen and B is —CH—, and an insecticidally and miticidally acceptable adjuvant.

4. The insecticidal and miticidal composition according to claim 3, wherein $R^1$ is methyl group; $R^2$ represents hydrogen atom, $C_1$-$C_4$ alkyl group or $C_1$-$C_3$ alkoxy group; X represents hydrogen atom, halogen atom, $C_1$-$C_4$ alkyl group, $C_1$-$C_3$ alkoxy group or $C_1$-$C_3$ haloalkoxy group; $R^2$ and X may combine together to form:

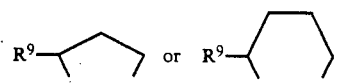

in which $R^9$ represents hydrogen atom or $C_1$-$C_3$ alkyl group; one of $R^6$ and $R^7$ represents hydrogen atom and the other represents hydrogen atom, methyl group, methoxy group or halogen atom; Y represents oxygen atom or carbonyl group and Z represents oxygen atom.

5. A method for controlling insects and mites, which comprises applying an insecticidally and miticidally effective amount of a pyrazole amide represented by the formula (I):

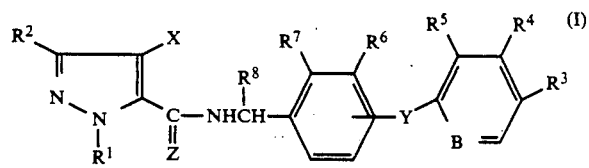

where $R^1$ represents $C_1$-$C_4$ alkyl group; $R^2$ represents hydrogen atom, $C_1$-$C_4$ alkyl group, cyclopropyl group, $C_1$-$C_4$ alkoxy group or $C_2$-$C_4$ alkylcarbonyloxy group; X represents hydrogen atom, halogen atom, $C_1$-$C_4$ alkyl group, $C_1$-$C_4$ alkoxy group, $C_1$-$C_3$ haloalkoxy group, $C_2$-$C_4$ alkylcarbonyloxy group or hydroxy group; $R^2$ and X may combine together to form

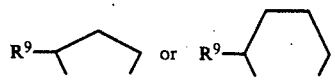

in which $R^9$ represents hydrogen atom or $C_1$-$C_3$ alkyl group; one of $R^3$, $R^4$ and $R^5$ is hydrogen atom and the others represent independently hydrogen atom, halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group or $C_3$-$C_6$ alkoxyalkoxyalkyl group; $R^3$ and $R^4$ may combine together to form

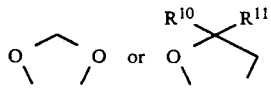

in which $R^{10}$ and $R^{11}$ represent independently hydrogen atom or $C_1$-$C_4$ alkyl group; one of $R^6$ and $R^7$ represents hydrogen atom and the other represents hydrogen atom, $C_1$-$C_4$ alkyl group, $C_1$-$C_4$ alkoxy group or halogen atom; Y represents oxygen atom, sulfur atom, sulfinyl group, sulfonyl group or carbonyl group; B represents —CH— or nitrogen atom; $R^8$ represents hydrogen atom or methyl group and Z represents oxygen atom or sulfur atom; with the proviso that all of $R^3$, $R^4$ and $R^5$ are not hydrogen atoms when Y is oxygen and B is —CH—, to eggs or larvae of the insects and mites.

6. The method according to claim 5, wherein $R^1$ is methyl group; $R^2$ represents hydrogen atom, $C_1$-$C_4$ alkyl group or $C_1$-$C_3$ alkoxy group; X represents hydrogen atom, halogen atom, $C_1$-$C_4$ alkyl group, $C_1$-$C_3$ alkoxy group or $C_1$-$C_3$ haloalkoxy group; $R^2$ and X may combine together to form:

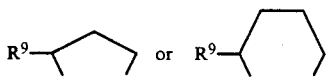

in which $R^9$ represents hydrogen atom or $C_1$-$C_3$ alkyl group; one of $R^6$ and $R^7$ represents hydrogen atom and the other represents hydrogen atom, methyl group, methoxy group or halogen atom; Y represents oxygen atom or carbonyl group and Z represents oxygen atom.

7. The pyrazole amide according to claim 1, wherein one of $R^3$, $R^4$ and $R^5$ is halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group or $C_3$-$C_6$ alkoxyalkoxyalkyl group.

8. The insecticidal and miticidal composition according to claim 3, wherein one of $R^3$, $R^4$ and $R^5$ is halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group or $C_3$-$C_6$ alkoxyalkoxyalkyl group.

9. The method according to claim 5, wherein one of $R^3$, $R^4$ and $R^5$ is halogen atom, $C_1$-$C_4$ alkyl group, $C_1$-$C_4$ haloalkyl group, $C_3$-$C_6$ cycloalkyl group, $C_1$-$C_4$ alkoxy group, $C_1$-$C_4$ haloalkoxy group, amino group, $C_1$-$C_4$ alkylamino group, $C_2$-$C_6$ dialkylamino group, $C_2$-$C_5$ alkoxycarbonylamino group, $C_1$-$C_4$ alkylthio group, $C_1$-$C_4$ alkylsulfinyl group, $C_1$-$C_4$ alkylsulfonyl group, $C_2$-$C_5$ alkoxycarbonyl group, $C_2$-$C_5$ alkylcarbonyl group, nitro group, cyano group, hydroxymethyl group, $C_2$-$C_4$ alkoxyalkyl group or $C_3$-$C_6$ alkoxyalkoxyalkyl group.

* * * * *

UNITED STATES PATENT AND TRADEMARK OFFICE
CERTIFICATE OF CORRECTION

PATENT NO. : 5,039,693

DATED : August 13, 1991

INVENTOR(S) : Itaru OKADA et al

It is certified that error appears in the above-identified patent and that said Letters Patent is hereby corrected as shown below:

In Column 28, line 33, "alkylcarbonyl" should read as

-- alkylcarbonyloxy --.

Signed and Sealed this

Second Day of February, 1993

Attest:

STEPHEN G. KUNIN

Attesting Officer

Acting Commissioner of Patents and Trademarks